United States Patent [19]

Kim

[11] Patent Number: 5,688,681
[45] Date of Patent: Nov. 18, 1997

[54] MONOCLONAL ANTIBODIES TO HUMAN LEUKEMIA INHIBITORY FACTOR

[75] Inventor: Kyung Jin Kim, San Francisco, Calif.

[73] Assignee: Genentech, Inc., South San Francisco, Calif.

[21] Appl. No.: 258,918

[22] Filed: Jun. 13, 1994

Related U.S. Application Data

[63] Continuation of Ser. No. 56,966, Apr. 29, 1993, abandoned, which is a continuation of Ser. No. 880,400, May 8, 1992, abandoned.

[51] Int. Cl.$^6$ .......................... C07K 16/24; C12P 21/08; C12N 5/20; G01N 33/53
[52] U.S. Cl. .......................... 435/240.27; 530/388.23; 435/7.1
[58] Field of Search ............... 530/388.23, 391.7; 435/240.27, 7.1; 424/145.1, 178.1, 183.1

[56] References Cited

U.S. PATENT DOCUMENTS

| | | | |
|---|---|---|---|
| 4,722,899 | 2/1988 | Hamaoka et al. | |
| 5,045,451 | 9/1991 | Uhr et al. | 435/7.23 |
| 5,106,951 | 4/1992 | Morgan et al. | 530/391.9 |

FOREIGN PATENT DOCUMENTS

WO13985  9/1991  WIPO.

OTHER PUBLICATIONS

Hilton & Gough, J. Cell. Biochem., 46:21–26 (1991).
Murphy et al., PNAS USA, 88:3498–3501 (1991).
Metcalf & Gearing, PNAS USA, 86:5948–5952 (1989).
Mori et al., BBRC, 160(3):1085–1092 (1989).
Reid et al; Endocrin., 126(3):1416–1420 (1990).
Maekawa & Metcalf, Leukemia, 3(4):270–276 (1989).
Allan et al, J. Cell Physiol., 145:110–119 (1990).
Yamamori et al., Science, 246:1412–1416 (1989).
Baumann & Wong, J. Immunol., 143:1163–1167 (1989).
Tomida et al., FEBS Letts., 151(2):281–285 (1983).
Rose & Bruce, PNAS USA, 88:8641–8645 (1991).
Gough et al., PNAS USA, 85:2623–2627 (1988).
Abe et al, PNAS USA, 83:5958–5962 (1986).
Ferrara et al., PNAS USA, 89:698–702 (1992).
Hilton et al., PNAS USA, 85:5971–5975 (1988).
Tomida et al., J. Biol. Chem., 259(17):10978–10982 (1984).
Gearing et al., Embo J., 6(3):3995–4002 (1987).
Tomida et al., FEBS Letts., 178(2):291–296 (1984).
Davies, Nature, vol. 289, pp. 12–13 (1981).
Seaver, Genetic Engineering News, pp. 10 and 21 (1994).
Waldmann, Science, vol. 252, pp. 1657–1662 (1991).
Harris et al. TIBTECH, vol. 11, pp. 42–44 (1993).
Borrebaeck, Journal of Immunological Methods vol. 123, pp. 157–165 (1989).

*Primary Examiner*—Paula K. Hutzell
*Assistant Examiner*—Nancy A. Johnson
*Attorney, Agent, or Firm*—Timothy E. Torchia, Ph.D.; Sean A. Johnston

[57] ABSTRACT

The invention relates to monoclonal antibodies to human leukemia inhibitory factor. The disclosed monoclonal antibodies are believed to recognize unique epitopes on hLIF and are useful in the treatment of conditions wherein the presence of hLIF causes or contributes to undesirable pathological effects, such as cachexia, dysregulated calcium metabolism, or excessive bone cell proliferation, and in the detection of hLIF, for example, in clinical samples or specimens.

13 Claims, 6 Drawing Sheets

5,688,681

MONOCLONAL ANTIBODIES TO HUMAN LEUKEMIA INHIBITORY FACTOR

CROSS REFERENCE TO RELATED APPLICATIONS

This application is a continuation of U.S. Ser. No. 08/056,966, filed Apr. 29, 1993, now abandoned which is a continuation of Ser. No. 07/880,400, filed May 8, 1992, now abandoned.

FIELD OF THE INVENTION

This application relates to hybrid cell lines (lymphocyte hybridomas) for the production of monoclonal antibodies to human leukemia inhibitory factor, to such homogeneous monospecific antibodies, and to the use of such antibodies for diagnostic and therapeutic purposes.

BACKGROUND OF THE INVENTION

Leukemia inhibitory factor (LIF) is a polypeptide with a broad range of biological effects. LIF was initially purified from mouse cells and identified on the basis of its ability to induce differentiation in and suppress the proliferation of the murine monocytic leukemia cell line M1. Tomida, et al., J. Biol. Chem. 259:10978–10982 (1984); Tomida, et al., FEBS Lett. 178:291–296 (1984). Human LIF (hLIF) subsequently was shown to have comparable effects on human HL60 and U937 cells, particularly when acting in collaboration with GM-CSF or G-CSF colony stimulating factors. Maekawa, et al. Leukemia 3:270–276 (1989).

LIF has been shown to exhibit a variety of biological activities and effects on different cell types. For example, it has been shown to stimulate osteoblast proliferation and new bone formation, Metcalf, et al., Proc. Nat. Acad. Sci., 86:5948–5952 (1989), as well as bone resorption, Abe, et al., Proc. Nat. Acad. Sci. 83:5958–5962 (1986); Reid, et al., Endocrinology 126:1416–1420 (1990), stimulate liver cells to produce acute phase plasma proteins, Baumann, et al., J. Immunol. 143:1163–1167 (1989), inhibit lipoprotein lipase, Mori, et al., Biochem. Biophys. Res. Commun. 160:1085–1092 (1989), stimulate neuronal differentiation and survival, Murphy, et al., Proc. Nat. Acad. Sci. 88:3498–3501 (1991), Yamamori, et al., Science 246:1412–1416 (1989), and inhibit vascular endothelial cell growth, Ferrara, et al., Proc. Nat. Acad. Sci. 89:698–702 (1992). Receptors for LIF have been found on monocyte-macrophages, osteoblasts, placental trophoblasts, and liver parenchymal cells. Hilton, et al., J. Cell. Biochem. 46:21–26 (1991); Allan, et al., J. Cell. Physiol. 145:110–119 (1990); Hilton, et al., Proc. Nat. Acad. Sci. 85:5971–5975 (1988).

Depending upon its particular activity or effect, LIF has been referred to by various names, including differentiation-inducing factor (DIF, D-factor), hepatocyte-stimulating factor (HSF-II, HSF-III), melanoma-derived LPL inhibitor (MLPLI), and cholinergic neuronal differentiation factor (CDF). Hilton, et al., J. Cell. Biochem. 46:21–26 (1991).

Genomic and cDNA clones encoding murine, rat, and human LIF have been isolated. Gearing, et al., EMBO J. 6:3995–4002 (1987); Yamamori, et al., Science 246:1412–1416 (1989); Gough, et al., Proc. Nat. Acad. Sci. 85:2623–2627 (1988).

Antibodies to hLIF are expected to have valuable diagnostic and therapeutic applications, such as in assaying for the presence of hLIF in clinical specimens, and in regulating the biological effects of hLIF and the interaction of hLIF with its receptors and other ligands. In particular, monoclonal antibodies (mAbs) detecting unique epitopes of hLIF would be of great value in understanding and regulating the diverse biological activities of hLIF. Neutralizing mAbs specific for hLIF that inhibit one or more of the biological activities or effects of hLIF have great potential as therapeutic agents useful in the treatment of conditions wherein the presence of hLIF causes or contributes to undesirable pathological effects, such as cachexia, dysregulated calcium metabolism, or excessive bone resorption (such as may be associated with osteoporosis).

Several polyclonal antibodies have been described that react with LIF. Tomida, et al., FEBS Letters 151:281–285 (1983) immunized rabbits with partially purified D-factor from mouse cells, and obtained antibodies capable of neutralizing the activity of mouse D-factor, and to a lesser extent, rat and hamster D-factors, in several assays. Baumann, et al., J. Immunol. 143:1163–1167 (1989) reported that rabbit polyclonal antibodies against hepatocyte-stimulating factor III (HSF-III) neutralized the activity of hLIF on hepatic cells.

There is a need for high affinity monoclonal antibodies to hLIF that are capable of effective inhibition of the biological activities of hLIF. It would be particularly desirable to provide monoclonal antibodies that are effective inhibitors of hLIF binding to its receptors, but which do not interfere with the binding of other factors, such as interleukin 1 (IL-1), interleukin 3 (IL-3), interleukin 6 (IL-6), tumor necrosis factor-α (TNF-α), granulocyte CSF (G-CSF), granulocyte-macrophage-colony stimulating factor (GM-CSF), and Oncostatin M.

SUMMARY OF THE INVENTION

The present invention is based on successful research involving the production and extensive characterization of monoclonal antibodies to hLIF. Accordingly, the present invention is directed to monoclonal antibodies, and derivatives thereof, which are capable of recognizing unique epitopes on hLIF and/or which exhibit high affinity for hLIF. The invention is further directed to monoclonal antibodies capable of inhibiting one or more of the biological activities of hLIF.

In one aspect, the invention concerns an anti-hLIF monoclonal antibody that is capable of inhibiting the mitogenic effect of hLIF on leukemic cells, and that does not cross-react with IL-1, IL-3, IL-6, TNF-α, G-CSF, or GM-CSF.

In another aspect, the invention concerns isolated nucleic acid encoding such antibodies, and hybridoma or recombinant cells producing such antibodies.

In a further aspect, the invention concerns the therapeutic or diagnostic use of such antibodies. The monoclonal antibodies of the invention are useful as therapeutic agents, either by themselves or in conjunction with (chemo) therapeutic agents, to treat diseases or conditions that are aggravated by hLIF. The monoclonal antibodies of the invention also are useful in diagnostic and analytical assays for determining the presence of hLIF in clinical specimens.

These and further aspects will be apparent from the following detailed description.

DETAILED DESCRIPTION OF THE INVENTION

A. Definitions and General Methods

Figure 1:
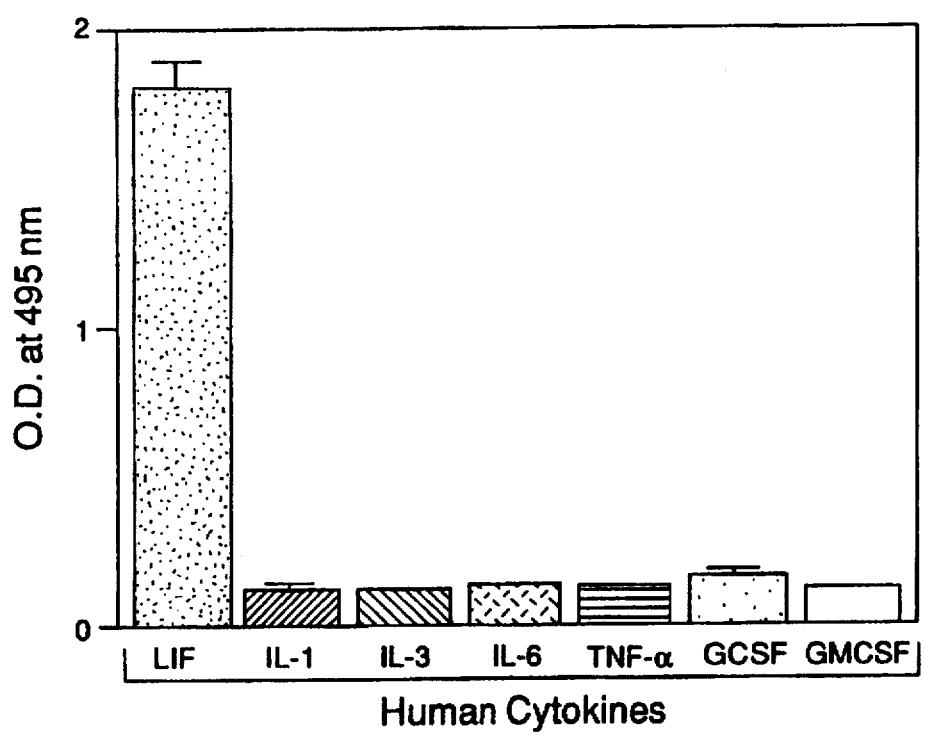
FIG. 1 shows the binding (antigenic) specificity of anti-hLIF mAb D25.1.4 as determined by ELISA.

The term "monoclonal antibody" as used herein refers to a substantially homogeneous population of antibodies, i.e., the individual antibodies comprising the population are identical in specificity and affinity except for possible naturally occurring mutations that may be present in minor amounts. Note that a monoclonal antibody composition may contain more than one monoclonal antibody.

The monoclonal antibodies included within the scope of the invention include hybrid and recombinant antibodies (for example, "humanized" antibodies) regardless of species of origin or immunoglobulin class or subclass designation, as well as antibody fragments (for example, Fab, F(ab')$_2$, and Fv), so long as they have the novel and unobvious characteristics of the antibodies described herein, in preferred embodiments being antibodies that are capable of binding to substantially the same epitope as one recognized by a monoclonal antibody produced by any one of the D3.14.1, D4.16.9, D25.1.4, or D62.3.2 hybridomas described herein, and/or that have affinity for that epitope which is greater than or equal to the affinity of a monoclonal antibody produced by any one of such hybridomas.

Thus, the modifier "monoclonal" indicates the character of the antibody as a substantially homogeneous population of antibodies, and is not to be construed as requiring production of the antibody by any particular method. For example, the monoclonal antibodies of the invention my be made using the hybridoma method first described by Kohler & Milsrein, Nature 256:495–497 (1975), or may be made by recombinant DNA methods. For example, see Cabilly, et al., U.S. Pat. No. 4,816,567; or Mage a Lamoyi, in *Monoclonal Antibody Production Techniques and Applications*, pp.79–97 (Marcel Dekker, Inc., New York, 1987).

In the hybridoma method, a mouse or other appropriate host animal is immunized with hLIF by subcutaneous, intraperitoneal, or intramuscular routes to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell. Goding, *Monoclonal Antibodies: Principles and Practice*, pp.59–103 (Academic Press, 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferass (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as P3-NS-1-Ag-4-1, Kohler, et al., Eur. J. Immunol 6:292–295 (1976), X63-Ag8.653, Kearney, et al., J. Immunol. 123:1548–1550 (1979), SP2/0-Ag/4, Sltulman, et al., Nature 276:269–270 (1978), or P$_3$X63Ag8U$_1$ Yelton et al., *Curr. Top. Microbiol. Immunol.* 81:1–7 (1978). Human myeloma and mouse-human heteromyeloma cell lines also have been described for the production of human monoclonal antibodies. Kozbor, J. Immunol. 133:3001–3005 (1984). Brodeur, et al., *Monoclonal Antibody Production Techniques and Applications*, pp. 51–63 (Marcel Dekker, Inc., New York, 1987).

Culture medium in which hybridoma cells are growing is conveniently assayed for production of monoclonal antibodies directed against hLIF. Preferably, the binding specificity of antibodies is determined by immunoprecipitation or by an in vitro binding assay, such as radioinimmunoassay (RIA) or enzyme-linked immunoabsorbent assay (ELISA), or by fluorescence activated cell sorting (FACS). The monoclonal antibodies of the invention are those that preferentially bind to soluble or cell bound hLIF and which are neutralizing, as explained herein. The specificity of binding of the monoclonal antibodies of the invention is determined by reaction of the antibodies with factors other than hLIF, with the objective being the identification of antibodies that do not bind to any factors other than hLIF, especially IL-1, IL-3, IL-6, G-CSF, GM-CSF, or Oncostatin M. A monoclonal antibody that preferentially binds to soluble or cell bound hLIF generally will exhibit at least the same degree of specificity of binding as a monoclonal antibody produced by any one of the D3.14.1, D4.16.9, D25.1.4, or D62.3.2 hybridomas described herein.

In a preferred embodiment of the invention, the monoclonal antibody will have an affinity which is greater than about $10^9$ liters/mole and preferably is equal to or greater than about $10^{10}$ liters/mole, as determined, for example, by the Scatchard analysis of Munson, et al., Anal. Biochem. 107:220–239 (1980).

The term "neutralizing antibody" as used herein refers to a monoclonal antibody that is capable of substantially inhibiting or eliminating a biological activity of hLIF.

After hybridoma cells are identified that produce neutralizing antibodies of the desired specificity and affinity, the clones typically are subcloned by limiting dilution procedures and grown by standard methods. Goding, *Monoclonal Antibodies: Principles and Practice*, pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the selected hybridoma cells are suitably purified from cell culture medium or ascites fluid by conventional immunoglobulin purification procedures such as, for example, protein A-SEPHAROSE, hydroxylapatite chromatography, gel electrophoresis, dialysis, or affinity chromatography.

DNA encoding the monoclonal antibodies of the invention is readily isolated and sequenced using conventional procedures (for example, by using oligonucleotide probes that are capable of binding specifically to genes encoding the heavy and light chains of murine antibodies). The hybridoma cells of the invention serve as a preferred source of such DNA. Once isolated, the DNA is ligated into expression or cloning vectors, which are then transfected into host cells such as simian COS cells, Chinese hamster ovary (CHO) cells, or myeloma cells that do not otherwise produce immunoglobulin protein. The transformant cells are cultured to obtain the synthesis of monoclonal antibodies in the recombinant host cell culture.

The DNA optionally is modified in order to change the character of the immunoglobulin produced by its expression. Immunoglobulin variants are well known. For example, chimeric antibodies are made by substituting the coding sequence for human heavy and light chain constant domains in place of the homologous murine sequences. Cabilly, et al., U.S. Pat. No. 4,816,567 et al.; Morrison, et al., Proc. Nat. Acad. Sci. 81:6851–6855 (1984). In addition, the Fc domain chosen is any of IgA, IgG-1, -2, -3 or -4. The Fc domain optionally is capable of effector functions such as complement binding.

Humanized forms of the murine antibodies are made by substituting the complementarity determining regions of the mouse antibody into a human framework domain, as described, for example, in U.S. patent application Ser. No. 07/715,272 now abandoned. In some embodiments, selected murine framework residues also are substituted into the human recipient immunoglobulin.

Fusions of the antibodies of this invention and cytotoxic moieties are made, for example, by ligating to the antibody coding sequence all or part of the coding sequence for a cytotoxic non-immunoglobulin polypeptide. Such non-immunoglobulin polypeptides include polypeptide toxins such as ricin, diphtheria toxin, or Pseudomonas exotoxin. Also, the conjugates can be prepared by in vitro methods. For example, immunotoxins may be constructed using a disulfide exchange reaction or by forming a thioether bond between the antibody and the toxin polypeptide. Examples of suitable reagents for this purpose include iminothiolate and methyl-4-mercaptobutyrimidate. Suitable fusion partners for the antibodies of this invention include viral sequences, cellular receptors such as the T-cell receptor, cytokines such as TNF, interferons, or interleukins, and other biologically or immunologically active polypeptides. Typically such non-immunoglobulin fusion polypeptides are substituted for the constant domains of an antibody of the invention. Alternatively, they are substituted for the variable domains of one antigen-combining site of an antibody of the invention.

Substitution of the Fc or complementary determining regions (CDRs) of an antibody having specificity for non-hLIF antigen will create a chimeric bivalent antibody comprising one antigen-combining site having specificity for hLIF and another antigen-combining site having specificity for a different antigen. In such embodiments, the light chain is deleted and the Fv domain of the heavy chain is substituted with the desired polypeptide. These antibodies are termed bivalent or polyvalent, depending upon the number of immunoglobulin "arms" possessed by the Fc domain employed (IgMs will be polyvalent). An antibody also may be rendered multivalent by intracellular recombination of antibodies having more than one specificity. For instance, an antibody in some embodiments is capable of binding hLIF as described elsewhere herein but is also capable of binding a T-cell, osteoblast, or liver cell surface antigen. In the case of T-cells, such antigens include CD3, CD4, CD8, CD18, CD11a, CD11b or CD11c. Examples of antibodies to cell surface antigens are well known. The multispecific, multivalent antibodies are made by cotransforming a cell with DNA encoding the heavy and light chains of both the anti-hLIF antibody and the anti-cell surface antigen antibody. Those expressed antibodies having the desired multispecific, multivalent structure then are recovered by immunoaffinity chromatography or the like. Alternatively, such antibodies are made from monovalent antibodies which are recombined in vitro in conventional fashion.

Monovalent antibodies also are made by techniques that are conventional per se. Recombinant expression of light chain and a modified heavy chain is suitable. The heavy chain is truncated generally at any point in the Fc region so as to prevent heavychain crosslinking. Alternatively, the relevant cystsines are substituted with another residue or deleted so as to prevent crosslinking. In vitro methods also are used to produce monovalent antibodies. For example, Fab fragments are prepared by enzymatic cleavage of intact antibody.

For diagnostic applications, the antibodies of the invention typically will be labeled with a detectable moiety. The detectable moiety can be any one which is capable of producing, either directly or indirectly, a detectable signal. For example, the detectable moiety my be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, for example, $^{125}I$, $^{32}P$, $^{14}C$, technicium, or $^3H$; or an enzyme, such as alkaline phosphatase, beta-galactosidase or horseradish peroxidase.

Any method known in the art for separately conjugating the antibody to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies of the present invention my be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be hLIF or an immunologically reactive portion thereof) to compete with the test sample analyte (hLIF) for binding with a limited amount of antibody. The amount of hLIF in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the invention also are useful for in vivo imaging, wherein an antibody labeled with a detectable moiety such as a radio-opaque agent or radioisotope is administered to a host, preferably into the bloodstream, and the presence and location of the labeled antibody in the host is assayed. This imaging technique is useful in the staging and treatment of neoplasms or bone disorders. The antibody may be labeled with any moiety that is detectable in a host, whether by nuclear magnetic resonance, radiology, or other detection means known in the art.

For therapeutic applications, the antibodies of the invention are administered to a mammal, preferably a human, in a pharmaceutically acceptable dosage form. They are administered intravenously as a bolus or by continuous infusion over a period of time, by intramuscular, subcutaneous, intra-articular, intrasynovial, intrathecal, oral, topical, or inhalation routes. When the antibody possesses the suitable activity it is also suitably administered by intratumoral, peritumoral, intralesional, or perilesional routes, to exert local as well as systemic therapeutic effects.

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffers such as phosphate or glycine, sorbic acid, potassium sorbate, partial glyceride mixtures of saturated vegetable fatty acids, water, salts, or electrolytes such as protamine sulfate, sodium chloride, metal salts, colloidal silica, magnesium trisilicate, polyvinyl pyrrolidone, cellulosic polymers, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. Conventional depot forms include, for example, microcapsules, nano-capsules, liposomes, plasters, sublingual tablets, and polymer matrices such as polylactide:polyglycolide copolymers. When present in an aqueous dosage form, rather than being lyophilized, the antibody typically will be formulated at a concentration of about 0.1 mg/ml to 100 mg/ml, although wide variation outside of these ranges is permitted.

For the prevention or treatment of disease, the appropriate dosage of antibody will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded herefrom.

According to another embodiment of the invention, the effectiveness of the antibody in preventing or treating disease may be improved by administering the antibody serially or in combination with another agent that is effective for the same clinical objective, such as another antibody directed against a different epitope than the principal antibody, or one or more conventional therapeutic agents known for the intended therapeutic indication, e.g. prevention or treatment of conditions associated with excessive bone resorption such as osteoporosis.

The antibodies of the invention also are useful as affinity purification agents. In this process, the antibodies against hLIF are immobilized on a suitable support, such a SEPHADEX resin or filter paper, using methods well known in the art. The immobilized antibody then is contacted with a sample containing the hLIF to be purified, and thereafter the support is washed with a suitable solvent that will remove substantially all the material in the sample except the hLIF, which is bound to the immobilized antibody. Finally, the support is washed with another suitable solvent, such as glycine buffer, pH 5.0, that will release the hLIF from the antibody.

The following examples are offered by way of illustration only and are not intended to limit the invention in any manner. All patent and literature references cited throughout the specification are expressly incorporated.

EXAMPLE 1

Preparation of Monoclonal Antibodies

Recombinant hLIF, Schmelzer, et al., Prot. Exp. Purificat. 1:54–62 (1990), was conjugated to keyhole limpet hemocyanin (KLH) according to the method of Nicolson, et al. Proc. Nat. Acad. Sci. 68:942 (1971). Balb/c mice were injected intraperitoneally with 10 µg of the resulting KLH-hLIF conjugate three times at two week intervals, and were boosted with the same dose of KLH-hLIF conjugate four days prior to cell fusion.

Spleen cells from the immunized mice were fused with $P_3X63Ag8U_1$ myeloma cells, Yelton, et al., Curr. Top. Microbiol. Immunol. 81:1–7 (1978), using 35% polyethylene glycol (PEG) as described. Laskov, et al., Cell. Immunol. 55:251–264 (1980). Hybridomas were selected in HAT medium.

Supernatants from hybridoma cell cultures were screened for anti-hLIF antibody production by an ELISA assay using hLIF-coated microtiter plates. Antibody that was bound to hLIF in each of the wells was determined using alkaline phosphatase-conjugated goat anti-mouse IgG immunoglobulin and the chromogenic substrate p-nitrophenyl phosphate. Harlow & Lane, *Antibodies: A Laboratory Manual*, p.597 (Cold Spring Harbor Laboratory, 1988). Hybridomas thus determined to produce anti-hLIF monoclonal antibodies were subcloned by limiting dilution.

Initially, 65 hybridomas producing anti-hLIF monoclonal antibodies were identified by ELISA. Of those, four hybridomas, designated D3.14.1, D4.16.9, D25.1.4, and D62.3.2 were chosen for further characterization. Ascites were produced in Balb/c mice and monoclonal antibodies were purified using protein-G conjugated 4B SEPHAROSE. Hereinafter, the monoclonal antibodies produced by the D3.14.1, D4.16.9, D25.1.4, and D62.3.2 hybridomas (designated ATCC accession no. HB 11076, ATCC accession no. HB 11077, ATCC accession no. HB 11074, and ATCC accession no. HB 11075, respectively, and deposited on Jun. 23, 1992, with the American Type Culture Collection, 12301 Parklawn Drive, Rockville, Md., USA) are referred to as mAb D3.14.1, mAb D4.16.9, mAb D25.1.4, and mAb D62.3.2, respectively.

EXAMPLE 2

Characterization of Monoclonal Antibodies

A. Antigen Binding Specificity

The binding specificities of the anti-hLIF monoclonal antibodies produced by the D3.14.1, D4.16.9, D25.1.4, and D62.3.2 hybridomas were determined by ELISA. 10 µg/ml of purified monoclonal antibody was added to the wells of microtiter plates that previously had been coated with 2 µg of hLIF, human IL-1, human IL-3, human IL-6, human TNF-α, human G-CSF, human GM-CSF, or human Oncostatin M. IL-6, G-CSF, and Oncostatin M are known to share significant amino acid sequence homologies with hLIF. Rose, et al., Proc. Nat. Acad. Sci. 88:8641–8645 (1991).

Bound antibody was detected with horse radish peroxidase (HRP) conjugated goat anti-mouse IgG immunoglobulins. The HRP color reaction was developed by the addition of phosphate buffered saline (PBS) containing 0.4 mg/ml. of o-phenylenediamine diamine dihydrochloride plus 0.4 µl/ml 30% hydrogen peroxide. The reaction was stopped by the addition of 100 µl/well 2.25M sulfuric acid. The color reaction was measured at 490 nm with an ELISA plate reader.

The results of those assays showed that each of mAb D3.14.1, mAb D4.16.9, mAb D25.1.4, and mAb D62.3.2 binds to hLIF, and not appreciably to those other protein factors, except that mAb D3.14.1 showed a weak cross-reactivity with human Oncostatin M. The results of the assay of mAb D25.1.4 reactivity with various protein factors are shown in FIG. 1. The other monoclonal antibodies showed similar binding specificity for hLIF.

Figure 2A:
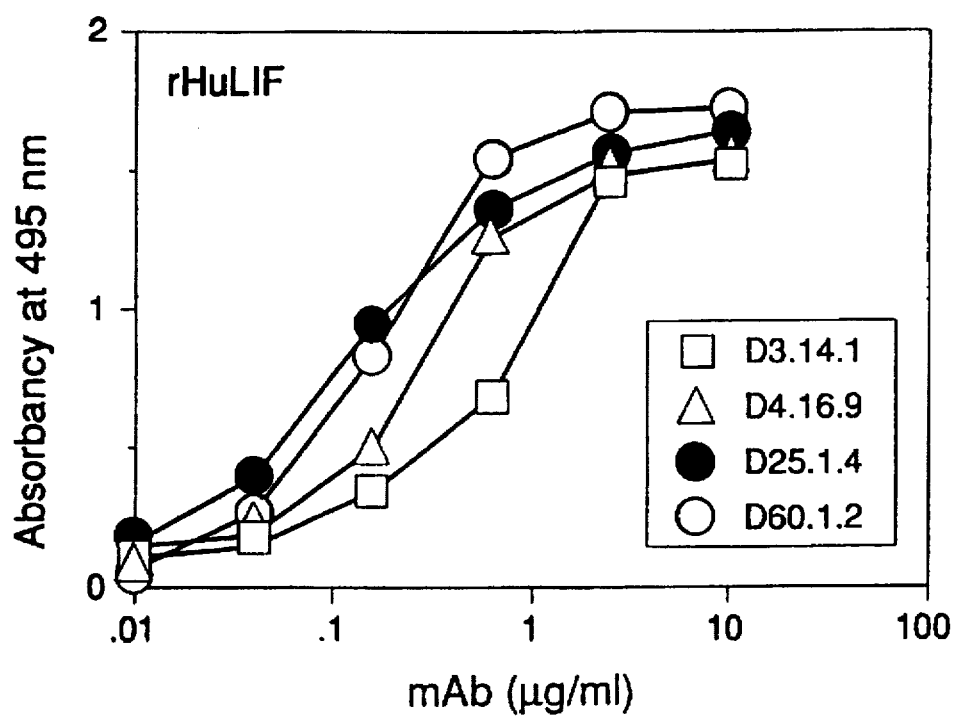
FIGS. 2A and 2B shows a comparison of the binding of anti-hLIF monoclonal antibodies to recombinant human LIF (rHuLIF) and recombinant murine LIF (rMuLIF) as determined by ELISA.
Figure 2B:
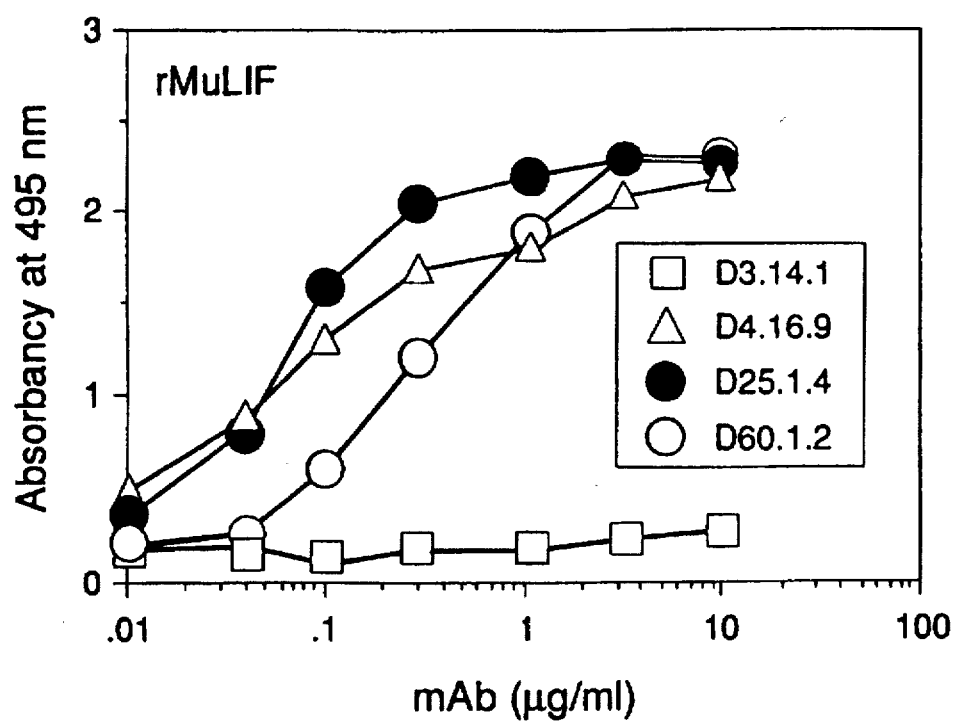

Additionally, the binding of mAb D3.14.1, mAb D4.16.9, mAb D25.1.4, and mAb D62.3.2 to murine LIF was determined by ELISA. As shown in FIGS. 2A–2B, mAb D4.16.9 and mAb D62.3.2 bound to murine LIF with about the same affinity as to hLIF, mAb D25.1.4 bound to murine LIF with lower affinity than to hLIF, and mAb D3.14.1 did not detectably bind to murine LIF.

B. Epitope Mapping

A competitive binding ELISA was used to determine whether the monoclonal antibodies produced by the D3.14.1, D4.16.9, D25.1.4, and D62.3.2 hybridomas bind to the same or different epitopes (sites) within hLIF. Anti-hLIF antibodies (mAb D3.14.1, mAb D4.16.9, mAb D25.1.4, and mAb D62.3.2) and an irrelevant anti-human vascular endothelial growth factor (hVEGF) antibody (mAb A3.13.1) were conjugated with horse radish peroxidase (HRP) and the competitive binding ELISA was performed as described by Kim, et al., Infect. Immun. 57:944–950 (1989).

Figure 3:
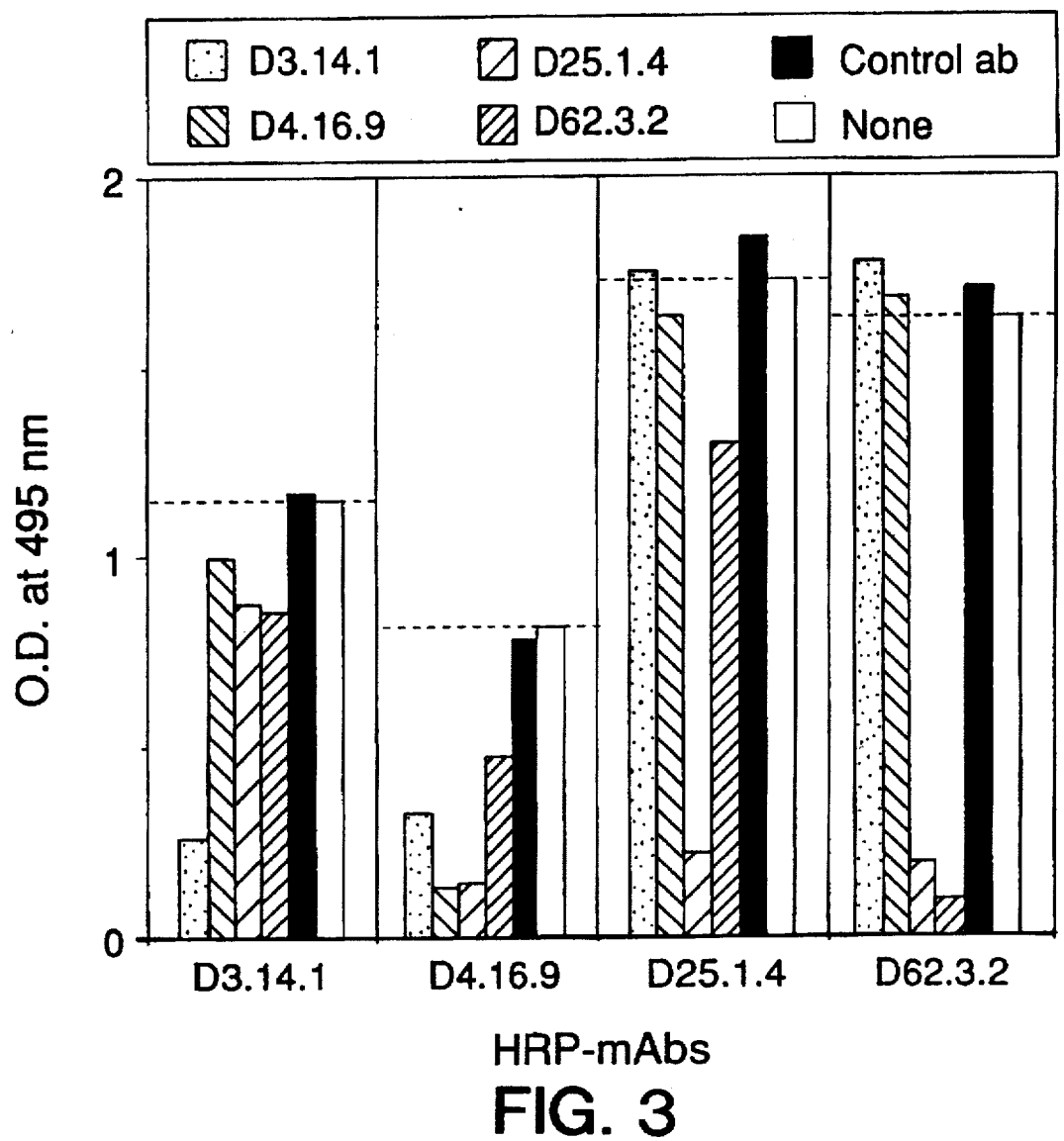
FIG. 3 shows the binding of horse radish peroxidase conjugated anti-hLIF monoclonal antibodies (HRP-mAbs) to hLIF in the presence and absence of 100-fold molar excess of unlabeled anti-hLIF monoclonal antibody (D3.14.1, D4.16.9, D25.1.4, or D62.3.2) or irrelevant control antibody (anti-hVEGF mAb A3.13.1).

As shown in FIG. 3, the inhibition pattern of the binding of each HRP-conjugated anti-hLIF antibody was unique, making it likely that each antibody recognizes a different epitope on hLIF. The binding of each of mAb D3.14.1 and mAb D25.1.4 was inhibited only by itself. The binding of mAb D4.16.4 was inhibited by mAb D3.14.1 and mAb D25.1.4 as well as mAb D4.16.4, while the binding of mAb D3.14.1 and mAb D25.1.4 was not blocked by mAb D4.16.9. The binding of mAb D62.3.2 was inhibited by mAb D25.1.4, but the binding of mAb D25.1.4 was not inhibited by mAb D62.3.2.

C. Isotyping

The isotypes of the anti-hLIF monoclonal antibodies produced by the D3.14.1, D4.16.9, D25.1.4, and D62.3.2 hybridomas were determined by ELISA. Hybridoma cell culture supernatants were added to the wells of microtiter plates that had previously been coated with hLIF. The captured anti-hLIF monoclonal antibodies were incubated with different isotype-specific alkaline phosphatase-conjugated goat anti-mouse immunoglobulins (Fisher Biotech, Pittsburgh, Pa. USA), and the binding of the conjugated antibodies to the anti-hLIF monoclonal antibodies was determined by the addition of p-nitrophenyl phosphate. The color reaction was measured at 405 nm with an ELISA plate reader.

By that method, the isotype of the monoclonal antibodies produced by each of the D3.14.1, D4.16.9, D25.1.4, and D62.3.2 hybridomas was determined to be IgG1.

D. Binding Affinity

The affinities of the anti-hLIF monoclonal antibodies produced by the D3.14.1, D4.16.9, D25.1.4, and D62.3.2 hybridomas were determined by a competitive binding assays. A predetermined sub-optimal concentration of monoclonal antibody was added to samples containing 20,000–40,000 cpm $^{125}$I-hLIF (1–2 ng) and various known amounts of unlabeled hLIF (1–1000 ng) in 0.2 ml. phosphate buffered saline (PBS) containing 0.5% bovine serum albumin (BSA) and 0.05% Tween 20. After 1 hour at room temperature, 100 µl of goat anti-mouse Ig antisera (Pel-Freez, Rogers, Ark. USA) were added, and the mixtures were incubated another hour at room temperature. Complexes of antibody and bound protein (immune complexes) were precipitated by the addition of 500 µl of 6% polyethylene glycol (PEG, mol. wt. 8000) at 4° C., followed by centrifugation at 2000×G. for 20 min. at 4° C. The amount of $^{125}$I-hLIF bound to the anti-hLIF monoclonal antibody in each sample was determined by counting the pelleted material in a gamma counter.

Affinity constants were calculated from the data by Scatchard analysis. Munson, et al., Anal. Biochem. 107:220 (1980). The affinity of each of mAb D3.14.1, mAb D4.16.9, mAb D25.1.4, and mAb D62.3.2 was determined to be in the range of about $1.4 \times 10^9$ liters/mole to $1.7 \times 10^{10}$ liters/mole.

F. Inhibition of hLIF Activity

The antibodies produced by the D3.14.1, D4.16.9, D25.1.4, and D62.3.2 were assayed for their ability to neutralize the ability of hLIF to inhibit growth of M1-T22 murine myeloid leukemic cells, Tomida, et al., Biochem. J. 176:655–669 (1978), and the ability of hLIF to induce release of intracellular calcium ($Ca^{2+}$) from Jurkat human T-cells. M1-T22 is a subclone of the murine myeloid leukemia cell line M1. Tomida, et al., Biochem. J. 176:655–669

(1978). Jurkat human T-cells were originally described by Weiss, et al., J. Immunol. 133:123–128 (1984). The Jurkat human T-cells used in the assays described herein were from a stock maintained at Genentech, Inc.

The M1-T22 cell growth inhibition assay was carried out as described by Lowe, et al., DNA 8:351–359 (1989). Generally, M1-T22 cells at 104 cells/were suspended in the wells of microtiter plates in minimal essential medium (MEM) supplemented with 10% fetal calf serum (FCS), 2 mM nonessential amino acids, 1 mM sodiumpyruvate, 1 mM glutamine, penicillin, and streptomycin, in the presence of 0.1–0.2 ng/ml recombinant hLIF, with or without added anti-hLIF monoclonal antibodies (at 5×, 25×, or 125× molar excess relative to hLIF).

Figure 4:
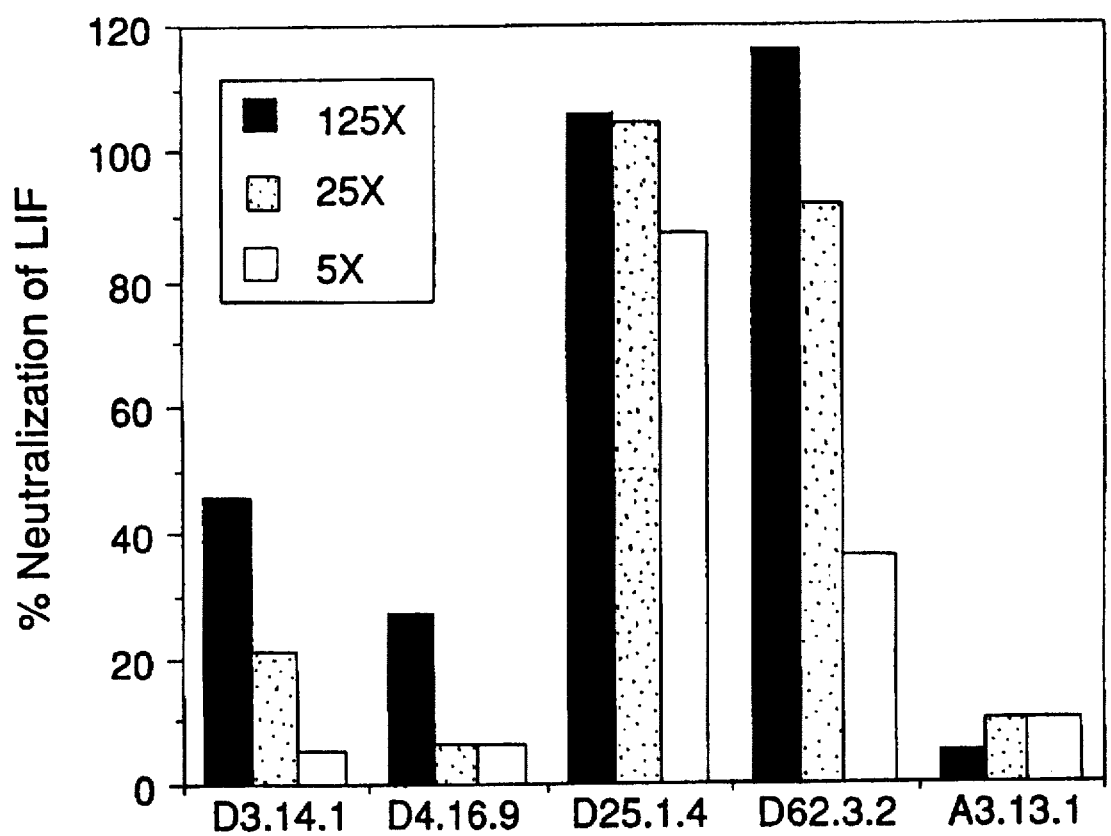
FIG. 4 shows the effect of anti-hLIF monoclonal antibody (D3.14.1, D4.16.9, D25.1.4, or D62.3.2) or irrelevant control antibody (anti-hVEGF mAb A3.13.1) on hLIF inhibition of M1-T22 murine myeloid leukemic cell growth. Results are expressed as a percentage reduction (neutralization) of such hLIF activity as compared to a control assay in which hLIF inhibition of M1-T22 murine myeloid leukemic cell growth was determined in the absence of antibody.
Figure 5:
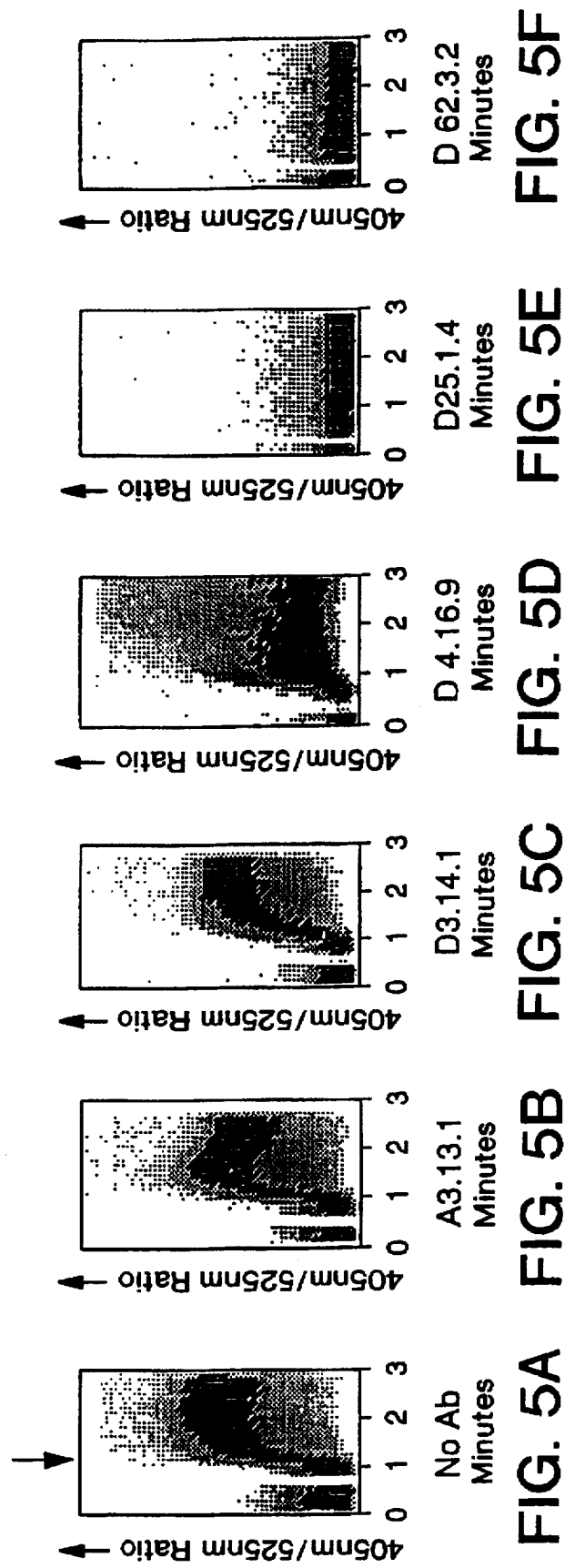
FIGS. 5A–5F shows fluorescence activated cell sorting (FACS) analysis of intracellular $Ca^{2+}$ levels in Jurkat human T-cells exposed to hLIF alone (no Ab), or hLIF pre-incubated with anti-hLIF monoclonal antibody (D3.14.1, D4.16.9, D25.1.4, or D62.3.2) or irrelevant control antibody (anti-hVEGF mAb A3.13.1). The assay was carried out over three minutes time; hLIF alone or the pre-incubated mixtures of hLIF and antibody were added one minute after the start of the FACS analysis (in the first panel (no Ab), for example, the time of addition of hLIF is indicated by the downward pointing arrow).

As shown in FIG. 4, mAb D25.1.4 blocked up to 87% of the M1-T22 growth inhibition activity of hLIF at a 1:5 molar ratio of antigen to antibody. mAb D25.1.4 blocked up to 90% of the M1-T22 growth inhibition activity of hLIF at a 1:25 molar ratio of antigen to antibody. mAb D3.14.1 and mAb D4.16.9 only minimally blocked the M1-T22 growth inhibition activity of hLIF.

In the course of making the present invention, it was found that hLIF induces an increase in cytoplasmic calcium ($Ca^{2+}$) concentration in Jurkat human T-cells. To determine the ability of anti-hLIF monoclonal antibodies to inhibit that activity of hLIF, Jurkat human T-cells at $10^6$ cells/ml were loaded with 5 µM indo-1 acetoxymethylester, Grynkiewicz, et al., J. Biol. Chem. 260:3440–3450 (1985), for 15 minutes at 37° C. as described. June, et al., Pathol. Immunopatho. Res. 7:409–432 (1988). The cells were then washed with RPMI medium without $Ca^{2+}$ and $Mg^{2+}$, and resuspended in the same medium. 10 µl of anti-hLIF monoclonal antibody was incubated with 100 µl of hLIF (5 µg/ml) for one hour. hLIF alone or an antibody-hLIF mixture was then added to the indo-1 loaded Jurkat cell cultures. Immediately after, level of free cytosolic $Ca^{2+}$ in the cells was determined by fluorescence activated cell sorting, using a Coulter 753 cell sorter and 200 mW UV excitation (351.1–363.8 nm), with fluorescence emission collected as a ratio of 405 nm/525 nm as described by June, et al., Pathol. Immunopathol. Res. 1:409–432 (1988).

As shown in FIGS. 5A–5F, hLIF (not pre-incubated with antibody) induced an increase in intracellular $Ca^{2+}$ in the Jurkat cells within several minutes after its addition to the cell cultures. Preincubation of hLIF with any one of mAb D4.16.9, mAb D25.1.4, or mAb D62.3.3 reduced or eliminated the hLIF-induced increase in intracellular. $Ca^{2+}$. Preincubation of hLIF with mAb D3.14.1 had little or no effect on hLIF-induced increase in intracellular $Ca^{2+}$.

To determine the effect of the monoclonal antibodies on hLIF binding to its receptors, $^{125}$I-hLIF binding to M1-T22 cells was compared in the presence and absence of anti-hLIF monoclonal antibody. $^{125}$I-hLIF ($5\times10^4$ cpm/2 ng) was incubated with various amounts of antibody (either 1×, 10×, or 50× the molar amount of hLIF) in a final volume of 100 µl for 30 minutes at 37° C. $10^6$ M1-T22 cells were then added to the antibody-hLIF mixture and incubation continued for 30 minutes at 37° C. Unbound $^{125}$I-hLIF was separated from bound $^{125}$I-hLIF by loading the mixtures onto a solution of 20% sucrose, 0.1% bovine serumalbumin (BSA) in phosphate buffered saline (PBS) and centrifuging at 300×G for 10 minutes. The supernatant was removed and the radioactivity associated with the pellet was counted in a gamma counter.

Figure 6:
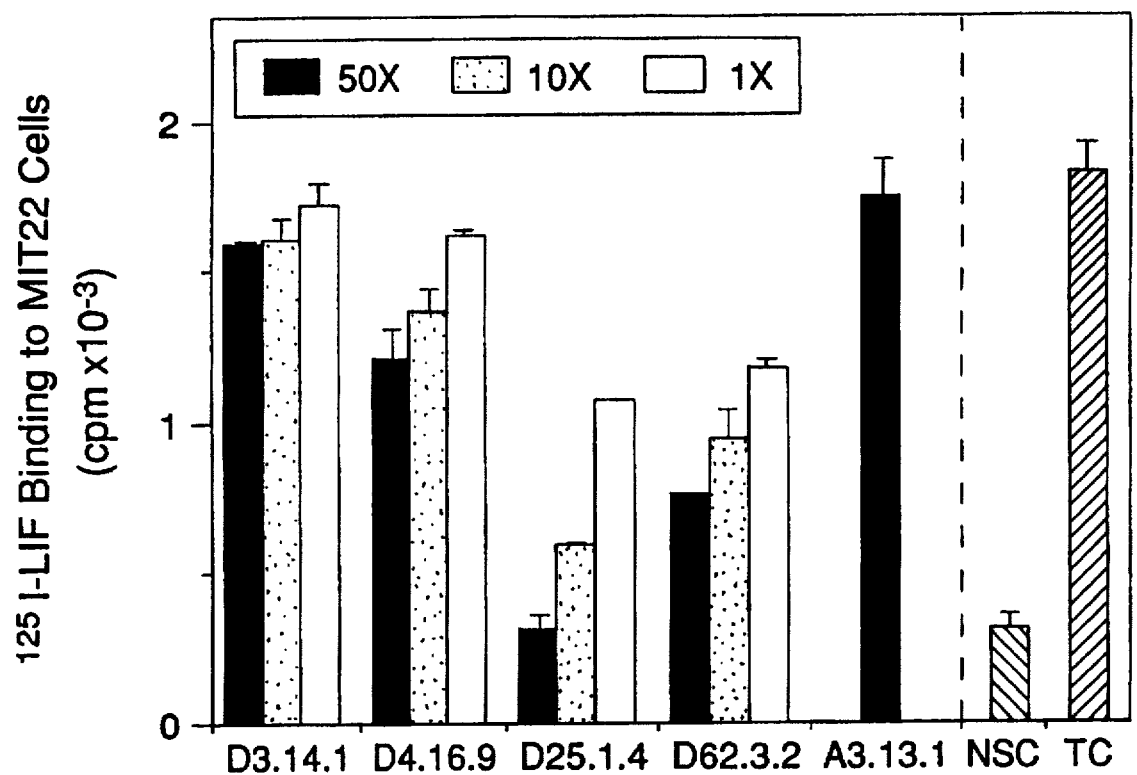
FIG. 6 shows the binding of $^{125}$I-hLIP to hLIF receptors on M1-T22 cells in the presence of unlabeled anti-hLIF monoclonal antibody (D3.14.1, D4.16.9, D25.1.4, or D62.3.2) or irrelevant control antibody (anti-hVEGF mAb 3.13.1). The amount of anti-hLIF monoclonal antibody added was either 50×, 10×, or 1× the molar amount of hLIF in the assay. NSC=$^{125}$I-hLIF bound to M1-T22 cells in the presence of 1000-fold molar excess of unlabeled hLIF (a measure of non-specific binding). TC=$^{125}$I-hLIF bound to M1-T22 cells in the absence of antibody (a measure of maximal binding).

As shown in FIG. 6, the anti-hLIF antibodies differed in their ability to block hLIF binding to its receptors. At a 50× molar excess of antibody to $^{125}$I-hLIF, mAb D25.1.4, mAb D62.3.2, mAb 3.14.1, and mAb 4.16.9 reduced $^{125}$I-hLIF binding by about 95%, 65%, 10%, and 30%, respectively. By comparison, $^{125}$I-hLIF binding to M1-T22 cells was reduced about 80% by the addition of a 1000-fold molar excess of unlabeled hLIF.

EXAMPLE 3

Use of Anti-HLIF Monoclonal Antibodies in ELISA to Detect Human LIF

Figure 7:
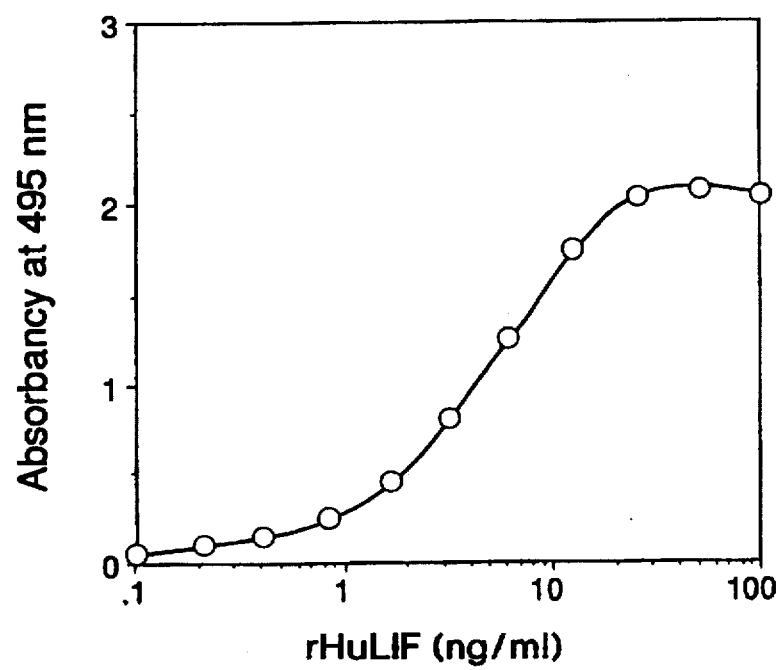
FIG. 7 shows the results of an ELISA for detection of various concentrations of hLIF, using mAb4.16.9 as a capture antibody and mAb 3.14.1 as a detection antibody.

To determine levels of hLIF in clinical or other samples, and to distinguish hLIF from other protein factors, an ELISA was developed using mAb 4.16.9 as a capture antibody and horse radish peroxidase-conjugated mAb 3.14.1 as a detection antibody. As shown in FIG. 7, using that combination of antibodies in an ELISA, as little as 0.1 ng hLIF could be detected.

What is claimed is:

1. A monoclonal antibody that specifically binds human LIF and neutralizes a biological activity of human LIF.

2. The monoclonal antibody of claim 1 wherein the monoclonal antibody is competitively inhibited in its binding to human LIF by a monoclonal antibody selected from the group consisting of monoclonal antibodies produced by hybridoma cells deposited under American Type Culture Collection Accession Numbers ATCC HB 11077, HB 11074, and HB 11075.

3. The monoclonal antibody of claim 2, which is capable of reducing the ability of hLIF to inhibit growth of M1-T22 murine myeloid leukemic cells, wherein the monoclonal antibody is competitively inhibited in its binding to human LIF by a monoclonal antibody selected from the group consisting of monoclonal antibodies produced by hybridoma cells deposited under American Type Culture Collection Accession Numbers ATCC HB 11074 and HB 11075.

4. The monoclonal antibody of claim 2, wherein the monoclonal antibody is competitively inhibited in its binding to human LIF by a monoclonal antibody selected from the group consisting of monoclonal antibodies produced by hybridoma cells deposited under American Type Culture Collection Accession Numbers ATCC HB 11074 and HB 11075.

5. The monoclonal antibody of claim 2 which has an affinity for hLIF of at least $10^9$ liters/mole.

6. A hybridoma cell which produces a monoclonal antibody of claim 2.

7. A hybridoma cell which produces a monoclonal antibody of claim 5.

8. The hybridoma cell deposited under American Type Culture Collection Accession Number ATCC HB 11077.

9. The hybridoma cell deposited under American Type Culture Collection Accession Number ATCC HB 11074.

10. The hybridoma cell deposited under American Type Culture Collection Accession Number ATCC HB 11075.

11. A monoclonal antibody produced by the hybridoma cell of claim 8.

12. A monoclonal antibody produced by the hybridoma cell of claim 9.

13. A monoclonal antibody produced by the hybridoma cell of claim 10.

* * * * *